(12) United States Patent
Flemming et al.

(10) Patent No.: US 8,076,162 B2
(45) Date of Patent: Dec. 13, 2011

(54) METHOD OF PROVIDING PARTICLES HAVING BIOLOGICAL-BINDING AREAS FOR BIOLOGICAL APPLICATIONS

(75) Inventors: Jeb H. Flemming, Albuquerque, NM (US); Colin T. Buckley, Albuquerque, NM (US); Carrie Schmidt, Las Lunas, NM (US)

(73) Assignee: Life Bioscience, Inc., Albuquerque, NM (US)

(*) Notice: Subject to any disclaimer, the term of this patent is extended or adjusted under 35 U.S.C. 154(b) by 0 days.

(21) Appl. No.: 12/419,899

(22) Filed: Apr. 7, 2009

(65) Prior Publication Data

US 2009/0258441 A1 Oct. 15, 2009

Related U.S. Application Data

(60) Provisional application No. 61/043,052, filed on Apr. 7, 2008.

(51) Int. Cl.
*G01N 33/552* (2006.01)

(52) U.S. Cl. ........................................ 436/527

(58) Field of Classification Search .............. None
See application file for complete search history.

(56) References Cited

U.S. PATENT DOCUMENTS

| 5,395,498 | A | * | 3/1995 | Gombinsky et al. | 204/464 |
| 5,850,623 | A | * | 12/1998 | Carman et al. | 702/28 |
| 5,998,224 | A | * | 12/1999 | Rohr et al. | 436/526 |
| 6,843,902 | B1 | * | 1/2005 | Penner et al. | 205/76 |
| 7,410,763 | B2 | * | 8/2008 | Su et al. | 435/6 |
| 2003/0228682 | A1 | * | 12/2003 | Lakowicz et al. | 435/287.2 |
| 2004/0171076 | A1 | * | 9/2004 | Dejneka et al. | 435/7.1 |
| 2005/0089901 | A1 | * | 4/2005 | Porter et al. | 435/6 |
| 2005/0170670 | A1 | | 8/2005 | King et al. | |
| 2006/0147344 | A1 | * | 7/2006 | Ahn et al. | 422/70 |
| 2006/0177855 | A1 | * | 8/2006 | Utermohlen et al. | 435/6 |
| 2007/0155021 | A1 | | 7/2007 | Zhang et al. | |
| 2008/0291442 | A1 | * | 11/2008 | Lawandy | 356/301 |
| 2009/0130736 | A1 | * | 5/2009 | Collis et al. | 435/213 |
| 2009/0182120 | A1 | * | 7/2009 | Utermohlen et al. | 530/344 |

FOREIGN PATENT DOCUMENTS

WO 2008/154931 A1 12/2008

OTHER PUBLICATIONS

Lakowicz, J.R., et al., "Advances in Surface-Enhanced Fluorescence," Journal of Fluorescence (2004), 14:425-441.
Lyon, L.A., et al., "Raman Spectroscopy," Anal Chem (1998), 70:341R-361R.
International Search Report and Written Opinion for PCT/US2009/039807 dated Nov. 24, 2009.
Perro, A., et al., "Design and synthesis of Janus micro- and nanoparticles," J Mater Chem (2005), 15:3745-3760.
Zhang, H., et al., Synthesis of Hierarchically Porous Silica and Metal Oxide Beads Using Emulsion-Templated Polymer Scaffolds, Chem Mater (2004), 16:4245-4256.

* cited by examiner

*Primary Examiner* — Ann Lam
(74) *Attorney, Agent, or Firm* — Chainey P. Singleton; Chalker Flores, LLP (57) ABSTRACT

The present invention includes micro-sphere composition, methods of making binding assays. The present invention also includes a micro-sphere for binding biological molecules without pretreatment. The micro-sphere includes a spherical glass substrate having one or more metal nanoparticle regions that are exposed from within the glass, wherein the micro-sphere is capable of binding biological molecules without pretreatment.

24 Claims, 8 Drawing Sheets

No processing

FIG. 7A

Expose

FIG. 7B

Expose, Bake

FIG. 7C

Expose, Bake and Etch

FIG. 7D

Expose, no Bake, Etch

FIG. 7E

No Expose, Bake, Etch

FIG. 7F

No Expose, Bake, no Etch

FIG. 7G

No Expose, No Bake, Etch

METHOD OF PROVIDING PARTICLES HAVING BIOLOGICAL-BINDING AREAS FOR BIOLOGICAL APPLICATIONS

CROSS-REFERENCE TO RELATED APPLICATIONS

This application claims priority to U.S. Provisional Application Ser. No. 61/043,052, filed Apr. 7, 2008, the contents of which is incorporated by reference herein in its entirety.

TECHNICAL FIELD OF THE INVENTION

The present invention relates in general to the field of biosensors useful for identifying the presence of a bio-molecule in a sample, and more specifically to particles capable of directly binding a wide variety of bio-molecules without the use of hybridizing reagents.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, this background describes particles capable of directly binding a wide variety of bio-molecules with and without the use of hybridizing reagents. One factor that currently affects the usefulness of many diagnostics is the rapid, selective, and sensitive detection of biochemical substances, e.g., proteins, metabolites, nucleic acids, biological compounds, etc. Another factor is that it is often necessary to identify and differentiate between a large number of biochemical constituents in complex samples.

Bioprobes are receiving increased emphasis by researchers since they overcome many of these limitations. Generally, these assays use fluorescent or chemiluminescent labels which have certain limitations, e.g., spectral specificity. For example, one spectroscopic technique, Raman spectroscopy, is a phenomenon observed in the scattering of light as it passes through a material medium so that the light experiences a change in frequency and a random alteration in phase. In so doing the scattered photons have the same energy (frequency) and, therefore, wavelength, as the incident photons; however, a small fraction of light is scattered at optical frequencies different from the frequency of the incident photons, i.e., the Raman effect. Raman scattering can occur with a change in vibrational, rotational or electronic energy of a molecule. In addition, Raman spectroscopy is complementary to fluorescence and has been used as an analytical tool; however, low sensitivity historically has limited its applications.

Recently, a technique associated with this phenomenon called surface-enhanced Raman scattering (SERS) spectroscopy has been used for molecules adsorbed on microstructures of metal surfaces. This enhancement embodies a microstructured metal surface scattering process which increases the intrinsically weak normal Raman scattering due to a combination of several electromagnetic and chemical effects between the molecules adsorbed on the metal surface and the metal surface itself.

SUMMARY OF THE INVENTION

The present invention provides particles with high surface areas that are capable of directly binding a wide variety of biomolecules without the use of hybridizing reagents. In addition, hybridizing reagents can be immobilized to the particle, which then can be used to immobilize the biomolecules of interest. For example, nitrocellulose could be immobilized upon the particle and then the nitrocellulose could be used to immobilize the biomolecule.

The present invention includes a method of providing a bead having discrete binding areas for biological-materials by preparing a glass bead substrate by at least one process step selected from the group consisting of: exposing the glass bead to an activating energy source; baking the glass bead having a glass transition temperature at a temperature above the glass transition temperature; etching at least a portion of the glass bead to expose metal nanoparticles from within the glass, wherein the metal nanoparticles have a range of diameters and are spaced from other metal nanoparticles by an average distance of at least one-half the midpoint of the diameter range; and the metal nanoparticles are less than approximately 300 nanometers in diameter; whereby the areas provide a chemistry for increased binding as compared to unselected areas.

The present invention also includes a micro-sphere for binding biological molecules without pretreatment. The micro-sphere includes a spherical glass substrate having one or more metal nanoparticle regions that are exposed within the glass, wherein the micro-sphere is capable of binding biological molecules without pretreatment.

In addition, the present invention includes a micro-sphere binding assay for binding biological molecules without pretreatment. The micro-sphere binding assay includes compositions and methods of making, using and preparing a micro-sphere bead substrate by at least one process step selected from the group consisting of exposing the glass micro-sphere bead to an activating energy source; baking the glass micro-sphere bead above the glass transition temperature; etching at least a portion of the glass micro-sphere bead to expose; and depositing patterned areas of biological-binding-glass on a substrate, wherein the metal nanoparticles have a range of diameters and are spaced from other metal nanoparticles by an average distance of at least one-half the midpoint of the diameter range, and the metal nanoparticles are less than about 300 nanometers in diameter, whereby the areas provide a chemistry for increased binding as compared to unselected areas; binding one or more biological molecules to the micro-sphere bead; and detecting the presence of the one or more biological molecules.

The present invention uses several inorganic binding mechanisms for binding. For example, the particles of the present invention include silver nanoparticles that contribute to a coordinated covalent binding of free thiols (cysteine) and amines (histidine). Another example of the binding mechanism of the present invention includes the hydrophobic interactions with the glass surface. Still other interactions include the hydrogen binding with free (OH— and COOH— moieties). In addition, the silver-fluoride dipole can aid in the biomolecule binding. Given the nature of the material, ionic interactions between the biomolecules and the glass are also available. The skilled artisan will recognize the present invention may be used to bind other molecules and/complexes, e.g., DNA, RNA, PNA, lipids, carbohydrates, ligands, receptors, pharmaceuticals, antigens, allergens, cells, antibodies, peptides, proteins, polymers, monomers, histones, other biomolecules, synthetic molecules and/or complexes.

The present invention includes distinct binding and non-binding regions of any shape and size, from 310 nm up to any desired size. In addition the present invention may be used for SEF, SERS, SPR, SEERS. In addition the imbedded nanoparticles of the present invention may be translated into other materials such as sol-gels, zeolites, hydrogels, and other glass or product formulations. The skilled artisan will recognize that common deposition techniques may be used in the present invention, e.g., CVD, electron beam, and so forth. In addition, the particles may be incorporated into common chromatography devices, such as microarrays, microfluidic channels, and chromatography columns.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present inventors recognized that there is great demand for rapid, simple, cost-effective technique for screening air, water complex cellular solutions and blood samples to identify various components therein, for example, medical diagnostics, drug discovery screening, genomics assays, proteomics analyses, detection of biological and chemical compounds and molecules and numerous other applications.

Figure 1A:
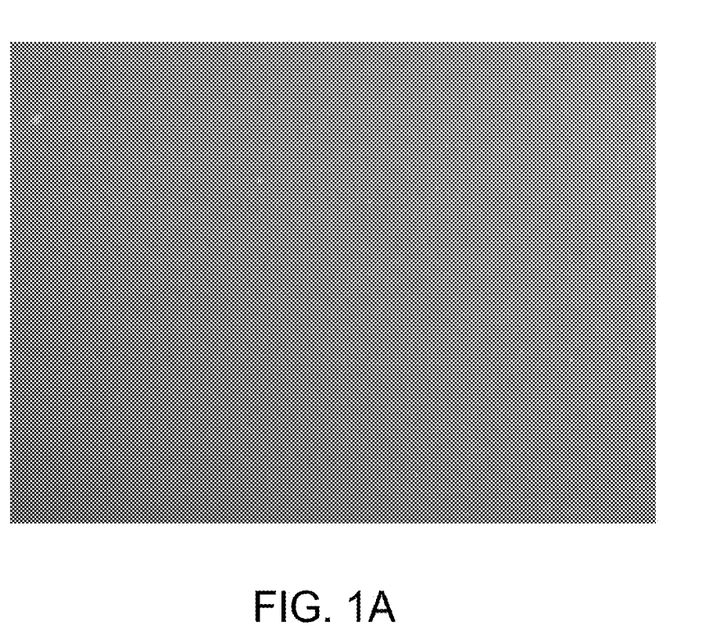
FIGS. 1A and 1B are images illustrating the fluorescence intensity of bound antibody fluorescence on the present invention (1A) and FOTURAN (1B)
Figure 1B:
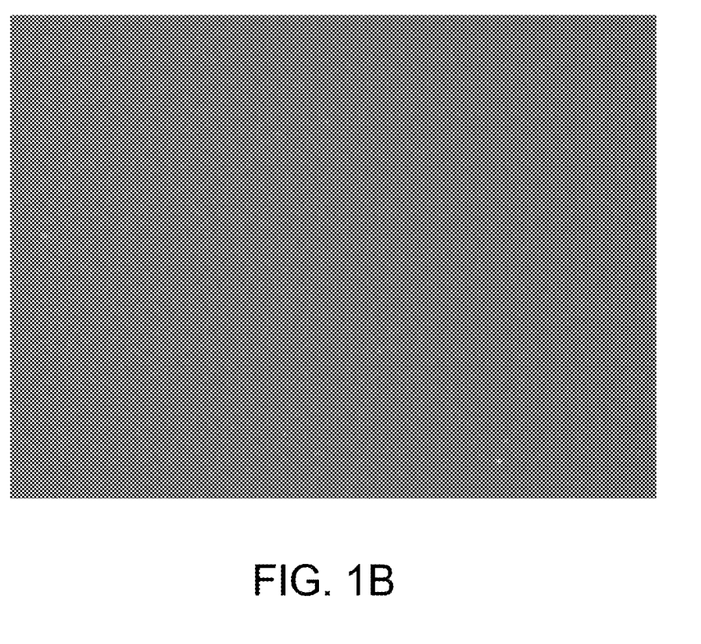

FIGS. 1A and 1B are images illustrating the fluorescence intensity of bound antibody fluorescence on the present invention as seen in FIG. 1A and a control FOTURAN sample as seen in FIG. 1B. FOTURAN is a limitedly available, commercial photoactive glass substrate. FIGS. 1A and 1B illustrate the present inventions ability to bind proteins. For example, rabbit IgG was contacted with the particles of the present invention for 45 minutes at 37° C. to immobilize the IgG on the surface. The sample was then rinsed and Rhodamine-labeled mouse anti-rabbit IgG was added to the sample for 45 minutes at 37° C. to immobilize the Rhodamine-labeled mouse anti-rabbit IgG. The sample was then washed and the fluorescence quantified using a fluorescent microscope. As seen in FIG. 1A the present invention provides greater fluorescence than the control FOTURAN sample. The greater fluorescence can be accounted for by the present invention providing more surface area for proteins to bind and/or the silver nanoparticles of the present invention provide a more appropriate configuration for Surface Enhanced Fluorescence.

Figures 2A, 2B, 2C:
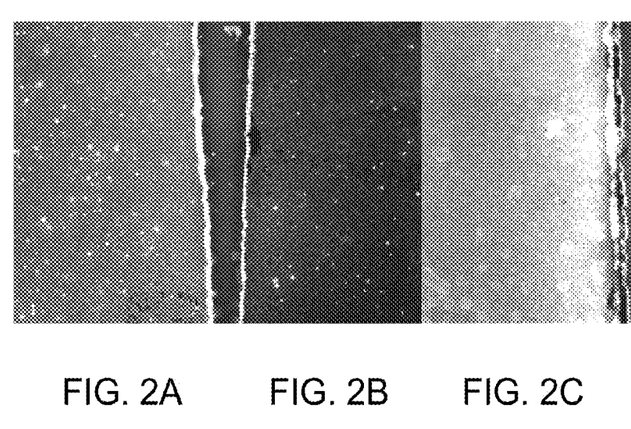
FIGS. 2A, 2B, 2C and 2D are images of the post process annealing of the present invention.
Figure 2D:
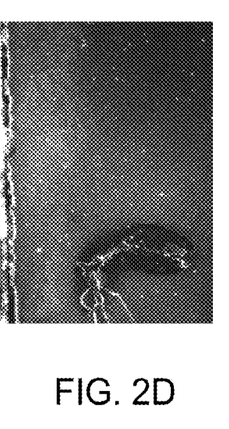

FIGS. 2A, 2B, 2C and 2D are images of the post process annealing of the present invention. FIGS. 2A and 2B are an image of the fluorescence of the present invention and a control after the post processing annealing. The sample of the present invention as seen in FIG. 2A was bake after the expose, bake, etch processing (baked at 500° C. for 6 hours). The negative controls were not annealed as seen in FIG. 2A. It is clear that the present invention has a greater fluorescence than the negative controls as seen in FIG. 2A. Similarly, the present invention has a greater fluorescence as seen in FIG. 2C than the negative controls as seen in FIG. 2D after being baked at 500° C. for 18 hours. The present invention has an increase in the detection of fluorescence from rhodamine PE, APC etc. labeled antibodies bound to the substrate. The increase in fluorescence is due to a change in the surface area or the silver is annealed together forming more appropriate nanoparticles that provide a surface enhanced fluorescence.

Figure 3A:
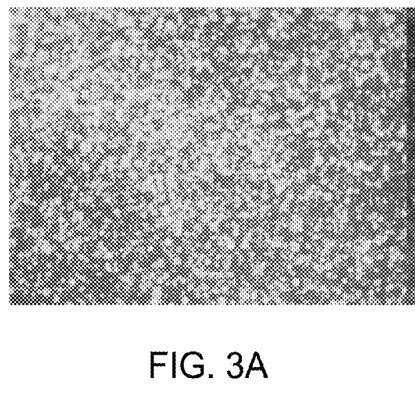
FIGS. 3A and 3B are fluorescence images of the unannealed (3A) and annealed (3B) beads of the present invention.
Figure 3B:
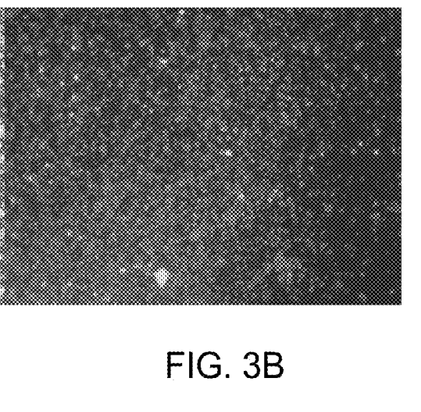

FIGS. 3A and 3B are fluorescence images of the unannealed as seen in FIG. 3A and annealed beads as seen in FIG. 3B of the present invention. FIG. 3A is a fluorescence image of the unannealed sample while FIG. 3B is an image of the annealed beads that were annealed above the glass transition point for 18 hours.

Figure 4A:
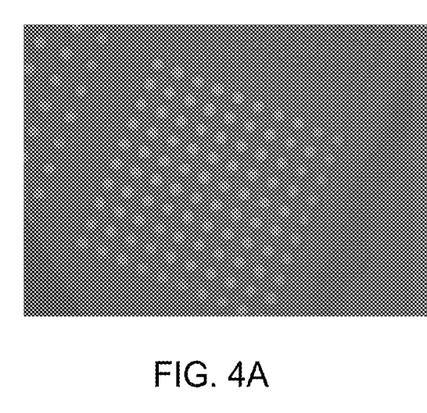
FIGS. 4A and 4B are fluorescence images of the peptide binding microarrays of the present invention.
Figure 4B:
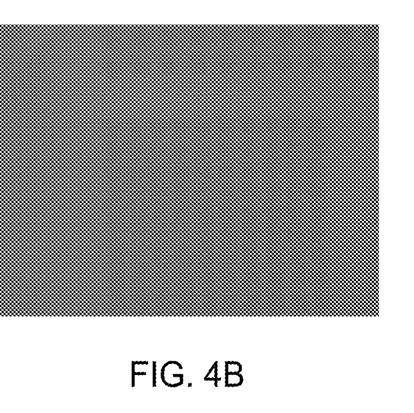

FIGS. 4A and 4B are fluorescence images of the peptide binding microarrays of the present invention. In general, peptides are notorious for their inability to be used in high throughput screening. The present invention provides a peptide binding microarray. The fluorescence images of FIGS. 4A and 4B are the result of a 4 step sandwich ELISA. As seen in FIG. 4A, a cysteine terminated peptide to the peptide binding microarray of the present invention. It is clear that the peptide binding microarray of the present invention illustrates FIG. 4A greater fluorescence than the comparably prepared control FIG. 4B. The present invention provides a peptide microarray platform for binding peptides using cysteine termination.

Figure 5A:
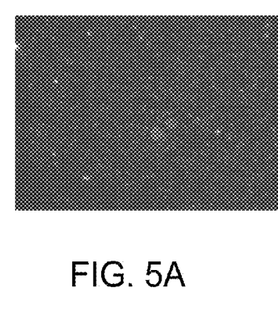
FIGS. 5A, 5B, 5C, 5D, 5E and 5F are fluorescence images of the affinity and the avidity of the beads of the present invention.
Figure 5B:
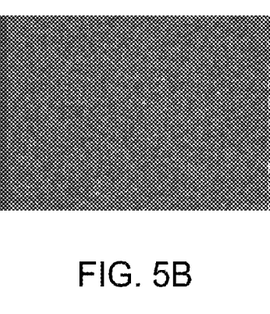
Figure 5C:
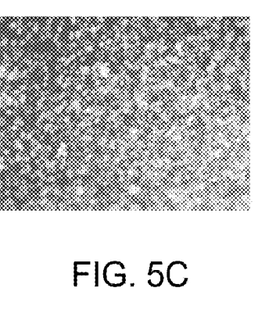
Figure 5D:
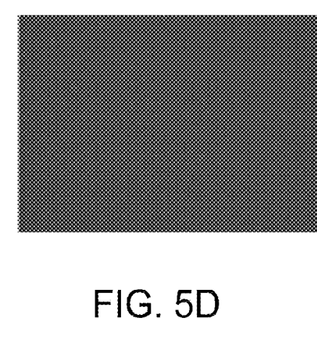
Figure 5E:
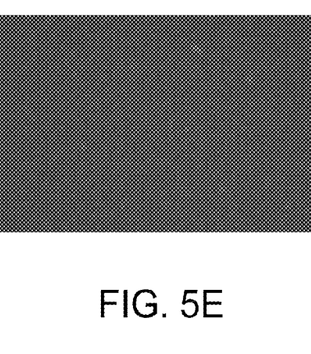
Figure 5F:
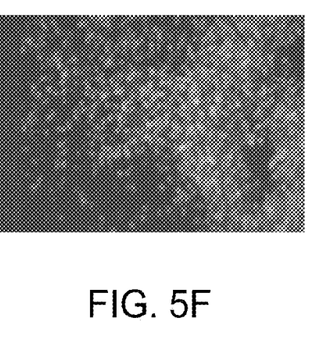

FIGS. 5A, 5B, 5C, 5D, 5E and 5F are fluorescence images of the affinity and the avidity of the beads of the present invention. Generally, avidity is a use to describe the combined strength of multiple bond interactions. This is distinct from affinity, which is a term used to describe the strength of a single bond. As such, avidity is the combined synergistic strength of bond affinities rather than the sum of bonds. For example, avidity is commonly applied to antibody interaction, where multiple, weak, non-covalent bonds form between antigen and antibody. Individually, each bond is quite readily broken, however when many are present at the same time the overall effect results in synergistic, strong binding of antigen to antibody. FIG. 5A is an image of polystyrene with the direct immobilization of goat anti-rabbit IgG, phycoerythrin conjugated. The beads were washed each day 4 times in 1 mL PBS and an aliquot of beads was removed and imaged with a 1 second exposure at day 0 in FIG. 5A and at day 3 in FIG. 5D. Similarly, an aliquot of silica beads were removed and imaged with a 1 second exposure at day 0 in FIG. 5B and at day 3 in FIG. 5E. In contrast, an aliquot of the beads of the present invention were removed and imaged with a 100 millisecond exposure at day 0 in FIG. 5C and at day 3 in FIG. 5F. It is clear that the present invention provided an increased fluorescence even given the shorter exposure time.

Figure 6A:
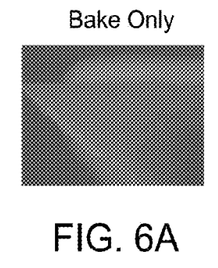
FIGS. 6A, 6B, 6C, 6D, 6E and 6F are fluorescence images of samples after processing.
Figure 6B:
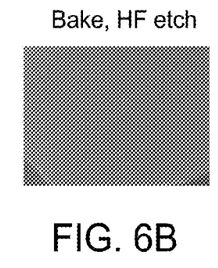
Figure 6C:
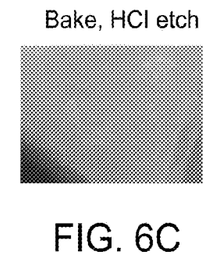
Figure 6D:
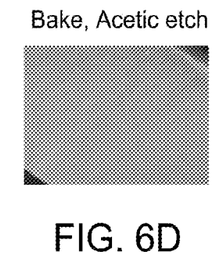
Figure 6E:
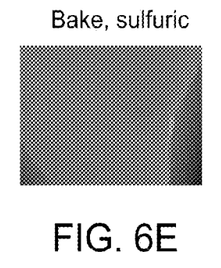
Figure 6F:
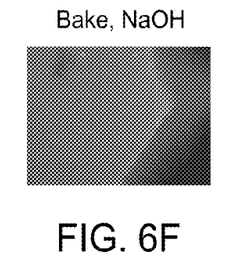

FIGS. 6A, 6B, 6C, 6D, 6E and 6F are fluorescence images of samples after processing. The samples are processed by the exposure of the beads to a high energy source and the beads are stirred in a fluidic medium during exposure, e.g., water. For example, a high powered collimated mid-UV light source. The noble metal oxide is converted into atomic noble metal. Noble metals include Cu, Ag, Au, and the metals in the platinum group. The beads are baked for 1 hour at 500° C. to allow the atomic silver to coalesce into nanoparticles of about 80 angstroms, and then the glass is baked for 1 hour at 600° C. to allow the lithium to coalesce around the silver to form a ceramic. The beads are etched in a basic or acidic solution to more appropriately activate the —OH groups on the bead surface. The fluorescence observed after the processing stated, and labeling with Phycoerythrin-labeled Antibody, and after all glass samples have been exposed. FIG. 6A is a fluorescence images of samples after processing that included baking only, FIG. 6B is a fluorescence images of samples after processing that included baking and HF etching, FIG. 6C is a fluorescence images of samples after processing that included baking and HCl etching, FIG. 6D is a fluorescence image of samples after processing that included baking and Acetic Acid etching, FIG. 6E is a fluorescence image of samples after processing that included baking and sulfuric acid etching and FIG. 6F is a fluorescence image of samples after processing that included baking and NaOH etching.

Figure 7A:
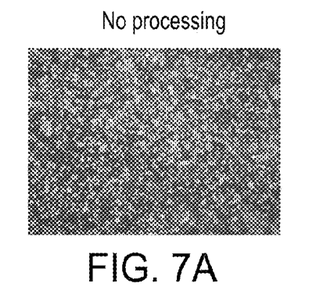
FIGS. 7A, 7B, 7C, 7D, 7E, 7F, 7G, and 7H are fluorescence images of samples after processing.
Figure 7B:
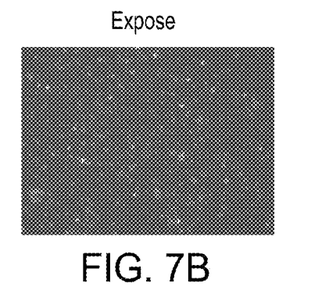
Figure 7C:
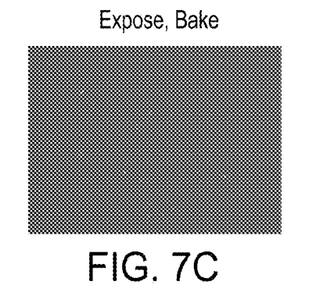
Figure 7D:
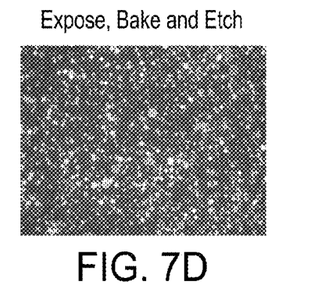
Figure 7E:
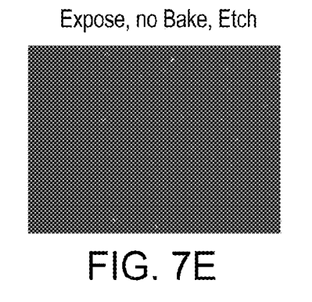
Figure 7F:
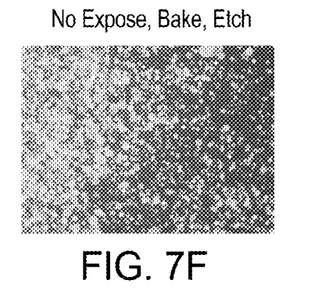
Figure 7G:
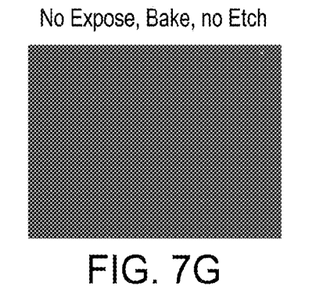
Figure 7H:
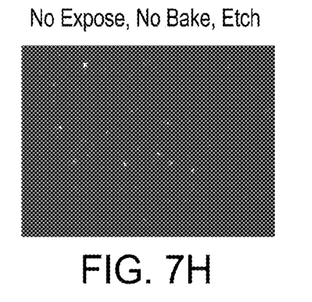

Similarly, FIGS. 7A, 7B, 7C, 7D, 7E, 7F, 7G, and 7H are fluorescence images of samples after processing. For example, the samples are processed by one or more of the following steps. When exposed, the exposure of the beads to a high energy source and the beads are stirred in a fluidic medium during exposure, e.g., water. When baked the beads are baked for 1 hour at 500° C. to allow the atomic silver to coalesce into nanoparticles of about 80 angstroms, and then the glass is baked for 1 hour at 600° C. to allow the lithium to coalesce around the silver to form a ceramic. The beads are then etched in a basic or acidic solution to more appropriately activate the —OH groups on the bead surface. The fluorescence observed was after the processing stated and labeling with Phycoerythrin-labeled Antibody, and all glass samples were exposed. FIG. 7A is a fluorescence image of samples after no processing, FIG. 7B is a fluorescence image of samples after processing that included exposing only, FIG. 7C is a fluorescence image of samples after processing that included exposing and baking, FIG. 7D is a fluorescence images of sample taken after processing that included exposing, baking and etching, FIG. 7E is a fluorescence image of samples after processing that included exposing and etching; and FIG. 7F is a fluorescence image of samples after processing that included baking and etching, FIG. 7G is a fluorescence image of samples after processing that included baking only, and FIG. 7H is a fluorescence image of samples after processing that included etching only.

The present invention provides that straight macromolecules bind to the surface of the particles of the present invention and are illustrated in the antibody matrix of binding of table 1 below. For example, straight macromolecules bind to the surface of the particles include Troponin I, ERK2, C-Reactive Protein, and phycoerythrin and peptides added to surface include: A PLC-gammal D-domain peptide (SEQ. ID. NO.: 1 RRKKIALELSELVVYC,) and a control sequence from PLC-gammal (SEQ. ID. NO.: 2 FLETNTLRTGERPELC)

| species | IgG | IgM | IgE |
|---|---|---|---|
| Mouse | Xxx | Xxx | |
| Rat | Xxx | | |
| Goat | Xxx | | |
| Bovine | xxx | | |

Figures 8A, 8B:
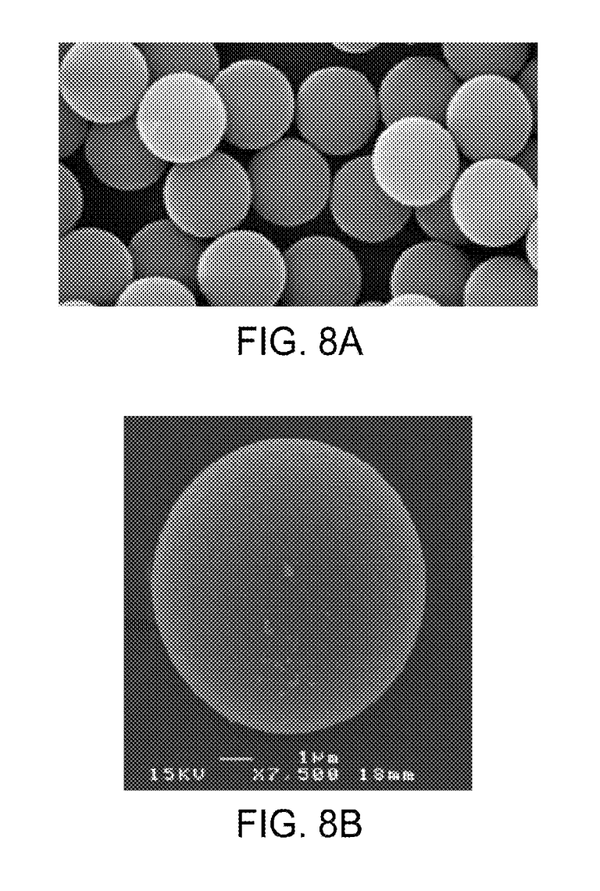
FIGS. 8A, 8B and 8C are particles images.
Figure 8C:
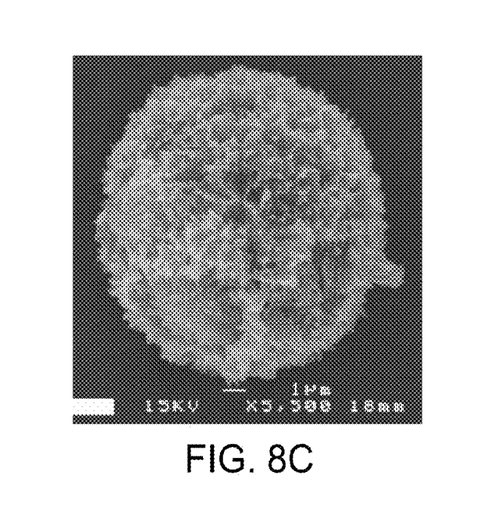

FIGS. 8A, 8B and 8C are particle images of the comparison beads and the beads of the present invention. FIG. 8A is an image of the beads of the control. FIG. 8B is a image of the beads of the present invention before processing, while FIG. 8C is an image of the beads of the present invention after processing. As illustrated in FIGS. 8B-8C, the present invention provides control of the surface and the surface area of the beads.

Figure 9A:
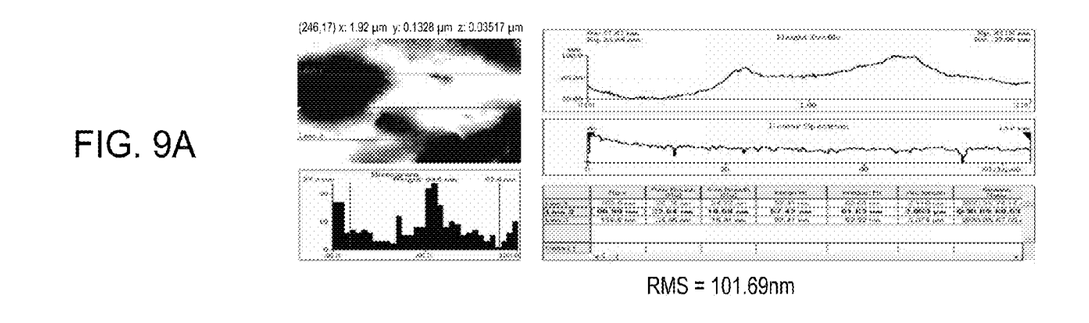
FIGS. 9A, 9B, 9C and 9D are plots of the unannealed surface and the annealed surface and their corresponding TEM images.
Figure 9B:
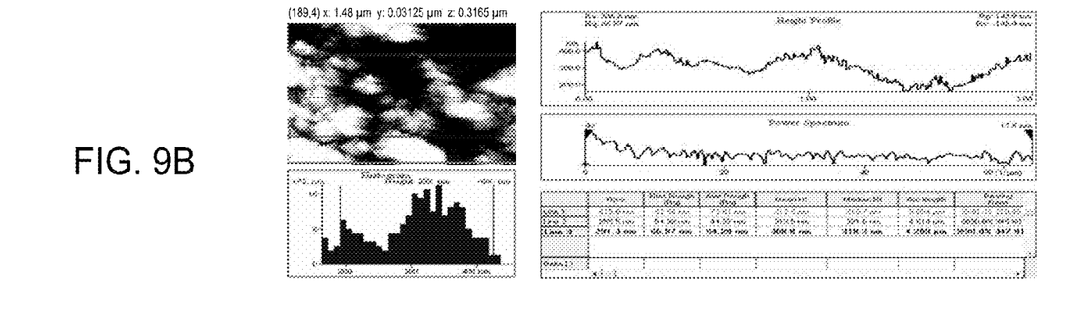
Figure 9C:
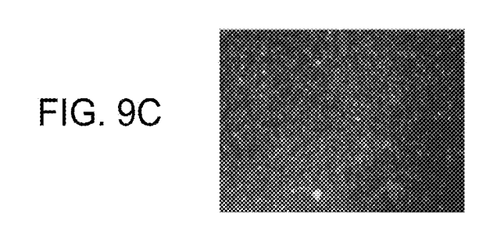
Figure 9D:
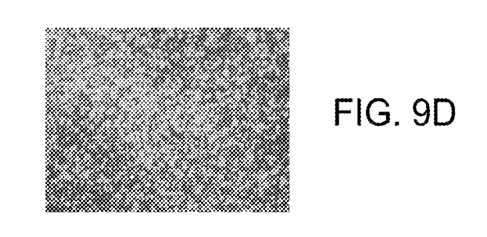

FIGS. 9A, 9B, 9C and 9D are plots of the unannealed surface and the annealed surface and their corresponding TEM images. FIGS. 9A and 9B are atomic force microscopy (AFM) data for the unannealed surface having a RMS of 101.69 nm and the annealed surface having a RMS of 67.05 nm. Annealing leads to increased fluorescence and a decreased bead surface area.

The present invention may be used in conjunction with glass that excites the surface plasmons of the noble metal content. As such the present invention may be used in SEF, SERS, SPR, SEERS, and other techniques that utilize altered states of noble metal plasmons for analytical techniques. The present invention may be used in conjunction with various different types of glasses that include glass-ceramics, e.g., lithium-alumino silicates and also Bioglass"45s5.

Generally, the glasses that possess imbedded noble metal nano-particles for SEF, SPR, SERS, etc. may be used with the present invention. In addition, the present invention may use a glass with a quantity of noble metal oxide. The present invention may also use a glass with a quantity of noble metal oxide that has such a large amount that of noble metal oxides that the glass strikes during cooling and nanoclusters of the said noble metal precipitate out within the glass. A glass with a quantity of noble metal oxide that also has cerium oxide present. The cerium oxide enables the reduction of the noble metal oxide to the atomic state. Further annealing allows the noble metals to coalesce. Furthermore, different annealing schedules may lead to different noble metal particle sizes. The cerium oxide approach enables the flood exposure for the whole glass with an activating energy source, such as ultraviolet light or protons to convert or the use of a photomask to pattern areas that can be converted. In addition, the glass may have a low glass transition temperature and/or solubility to the noble metal in the glass.

Figure 10A:
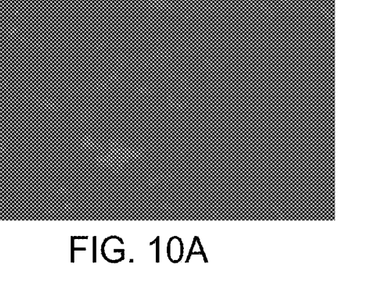
FIGS. 10A, 10B, 10C, 10D, 10E and 10F are images of the glass prepared using the present invention.
Figure 10B:
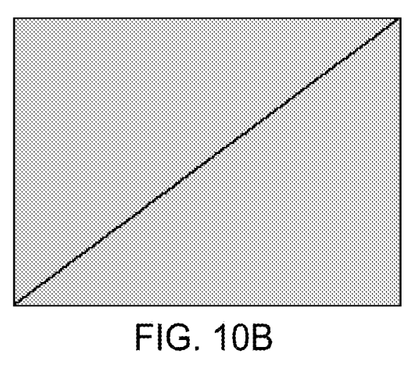
Figure 10C:
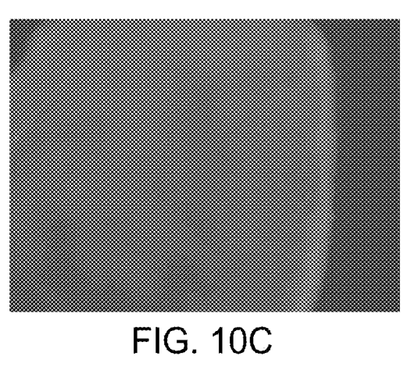
Figure 10D:
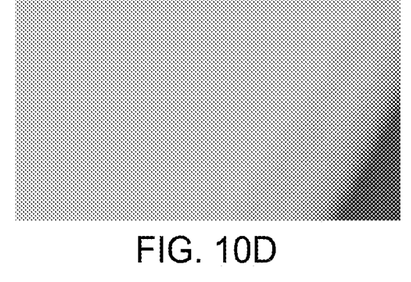
Figure 10E:
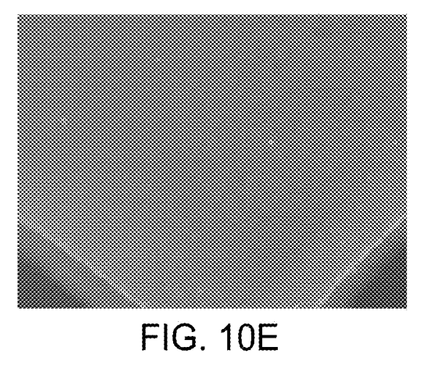
Figure 10F:
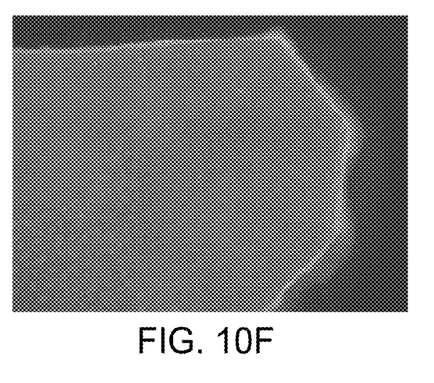

FIGS. 10A-10F are images of the glass prepared using the present invention. FIGS. 10A, 10B and 10C are images of the unprocessed glass, while the images 10D, 10E, and 10F correspond to the processed glass that was not exposed. The processed glass in FIGS. 10D, 10E, and 10F was baked at such a temperature to convert them into a ceramic and then etched with 20% HF for 3 minutes. All were immobilized with the same protein immobilization protocol as disclosed throughout the specification. It can be seen that both of the pictures without the noble metal nanoparticles do bind proteins better in the ceramic state than in the glass state. It can also be seen that the glass that contains the noble metal silver, fluoresces brighter. FIGS. 10A and 10D are images of glass 4 substrates either unprocessed or processed respectively. FIGS. 10B and 10E are images of glass 7KO substrates either unprocessed or processed respectively. FIGS. 10C and 10F are images of BIOGLASS 45S5 substrates either unprocessed or processed respectively. The present invention provides the addition of nucleating agents to the glass substrate to aid in the conversion of the glass form of a glass-ceramic to the ceramic phase. The nucleating agents aid in the transition of the substrate to a ceramic after a final heat treatment process. Such nucleating agents include: titanium dioxide, tin oxide, ruthenium, rhenium, oxmium iridum, phosphorous pentoxide, Vanadium pentoxide, molybdenum oxides, tungsten oxides, iron oxides and combinations thereof. In addition the skilled artisan will recognize that other nucleating agents and combinations of agents may be used, e.g., the glass substrate of the present invention may include silver, cerium and antimony.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The present invention provides method and compositions with discrete biological-binding areas within areas which minimize biological molecule binding. The biological-binding areas greatly enhanced biological molecule binding by fabricating areas which contain metal nanoparticles on and within a substrate. Biological molecules attach to the metal nanoparticles in these areas, which provide for increased biological molecule binding. The present invention provides surfaces which contain spaced metal nanoparticles in a glass matrix to greatly enhance biological molecule binding, as compared to identical immobilization protocols conducted on 99.99% pure silver wire surfaces.

The metal nanoparticles may include metals with the ability to bind non-bound electron pairs from molecules in solutions, e.g., high-protein (or other biological molecule(s))-affinity silver, gold, platinum, rhodium, palladium, cerium, nickel, cobalt, copper, or alloys containing these metals. The matrix containing the metal nanoparticles may be made from glass, plastics, or organic films, (e.g. nitrocellulous), polystyrene, sol-gels ceramics and/or combinations thereof. The present invention provides for spaced-apart metal nanoparticles which bind more biological molecules and greatly reduce biological molecule conformational distortion and thus greatly improves target molecule binding to biological molecule(s).

In addition, photoetchable glasses have been found to have several advantages for the fabrication of a wide variety of microsystems components. These glasses maybe constructed using conventional semiconductor processing equipment and are transparent in 400-1200 nm, possess high temperature stability, good mechanical properties, are electrically insulating, and have better chemical resistance than plastics and many metals to acids, bases, oxidizers, and solvents.

The present invention provides for the binding of biological molecules bound to surfaces through a variety of mechanisms. The metal nanoparticles directly bind several amino acid-containing molecules, such as proteins and peptides, in a coordinated-covalent bond; where D-orbitals of the metal nanoparticle bind free non-binding electrons on the biological molecule. A variety of amino acid side groups bind to the noble metal nanoparticles in this manner. Proteins are composed of 20 main amino acids. These amino acids have various side groups that contain compounds that can bind to noble metal nanoparticles in this manner.

Examples of some amino acids which may directly bind to the noble metal nanoparticles include: Arginine, Asparagine, Cysteine, Glutamine, Histadine, and Lysine. Therefore, thiol-groups in cysteine, amine groups in lysine, free herterocyclic aromatics (imidazole side chain) on histidine, and other capable moieties interact with the D-orbitals of the silver (noble metals or copper) nanoparticles forming a coordinated-covalent bond. This bond possesses a high bond energy, 51.9 kcal/mol for silver-thiol bonds, causing a nearly non-reversible binding event with the biomolecule. The noble metal nanoparticles bind nucleic acid molecules by binding the N7 position of guanine nucleotides found in nucleic acid-based molecules, such as DNA and RNA. Hydrophobic interactions within the glass and Hydrogen binding with free (OH— and COOH— moieties). Adsorption onto compounds present within the glass that are hydrophobic. During the etch process as fluoride ions from hydrofluoric acid remove silicon dioxide in the glass matrix, silver nanoparticles become exposed to the solution and fluoride ions bind to the silver nanoparticle; fluoride ions (Lewis base) may act as chemical ligands forming coordinated covalent bonds with metal cations (Lewis acid). This polar silver fluoride compound binds biomolecules through charged interactions. One embodiment of the present invention provides that cerium binds the proteins. Lithium aluminum hydroxide is produced during the processing of the glass. Lithium aluminum hydroxide is a powerful reducing agent in organic chemistry. The material may convert all $NH^{3+}$ side groups into $NH_2$, capable of binding to Noble metal nanoparticles, at a lower pH. Proteins like to be immobilized at their isoelectric point, which varies a lot from protein to protein. Therefore, the pH at which a protein is immobilized is very important in traditional immobilization chemistries.

In addition to the native binding mechanisms present above, the surface of the material may be modified in a variety of manners. For example, the material substrate may be functionalized with a variety of surface chemistries, such as amine groups, aldehyde groups, epoxy, avidin, strepavidin, nitrosylated polysaccharide, and other biological molecule binding chemistries to further capture biomolecules.

The metal nanoparticles can be of high-biological molecule-affinity silver, gold, platinum, rhodium, palladium, cerium, nickel, cobalt, copper, their alloys, or oxides of these elements. The matrixes can include glass, plastics, nitrocellulous, polystyrene, sol-gels, and/or ceramics, and in some embodiments even low-or-no-protein-affinity metals such as aluminum or zinc may be included for the matrix. For example, for proteins we use high-protein-affinity metal nanoparticles in a low-or-no-protein-affinity matrix. In some cases, we may have metal nanoparticles within a matrix of glass or ceramic, which is in turn within a matrix of, e.g., plastic.

One biological-binding glass has a composition comprising; less than 72% silica, at least 0.15% $Ag_2O$, at least 0.75% $B_2O_3$, at least 11% $Li_2O$, and at least 0.0014% $CeO_2$. Exposing at least one portion of the photosensitive glass substrate with ultraviolet light 240 to 360 (in some embodiments, 300 to 320) nm light or a directed source of protons using an activation exposure of 0.8-15 $J/cm^2$, while leaving at least a second portion of the glass wafer unexposed; heating the glass substrate to a temperature of 450-650° C., holding the glass substrate for at least ten minutes at a temperature of 450-650° C., and cooling the substrate to transform at least part of the exposed glass to a crystalline material; and etching the glass substrate in an HF-containing etchant solution.

The biological-binding areas for greatly enhanced biological molecule immobilization and detection may be accomplished using a photosensitive glass. With this glass areas which contain metal nanoparticles may be fabricated to control the areas which bind large amounts of biological molecules and which areas bind lower amounts. Additionally, photosensitive glass particles can be deposited on a substrate, through a variety of techniques, such as sol-gel processing, spin coating, thermal evaporation, etc., either in a pattern layer or an unpatterned layer. The glass particles may exist in a variety of form factors such as microspheres, thin films, microfibers, etc.

The metal nanoparticles are at least one of silver, gold, platinum, rhodium, palladium, nickel, cobalt, copper, or their alloys. In some embodiments, the biological-binding-areas are of a glass containing oxide of at least one of silver, gold, and copper, and wherein at least some of the oxide of at least one of silver, gold, and copper is reduced to metal to provide the metal nanoparticles. In some embodiments, the metal particles that are exposed from within the glass are formed by metal-precipitating and then metal-coalescing baking. In some embodiments, the areas are exposed by patterned high-energy particles (including UV light) to reduce at least some of the oxide of at least one of silver, gold, and copper in the areas to metal.

In some embodiments, at least one metal-coalescing baking step is done on glass micro-spheres, prior to screen printing of the glass micro-spheres on a substrate (e.g. with a sol-gel binder). In some embodiments, a surface activation etching after deposition on the substrate (alternatively in some cases, it is not used, and in still other cases it is used prior to deposition). In some embodiments, the metal particles are added as metal particles during fabrication of the biological-binding-material, rather than the currently generally preferred method of being reduced from an oxide or a salt. In some embodiments, the metal particles are added as metal salt during fabrication of biological-binding-glass. Further, in some embodiments, the matrix containing the metal particles is a non-glass (although still preferably transparent or translucent). In some embodiments, the micro-spheres are between 1 and 1,000,000 nanometers in diameter. In some embodiments, the metal particles are between 1 and 300 nanometers in diameter. In some embodiments, at least half the metal particles are 1-500 nanometers in diameter and spaced from other metal particles by an average distance of at least 2 nanometers. In some embodiments, at least half the metal particles are 1-500 nanometers in diameter and spaced from other metal particles by an average distance of at least 20 nanometers.

In some embodiments the biological-testing includes testing of at least one of DNA, RNA, and other nucleic acid containing molecules, PNAs, Amino acids, lipids, fatty acids, histones, proteins, peptides, and other amino acid containing molecules. In some embodiments, the biological-binding-organic contains at least one non-binding electron pair. In some embodiments, the metal particles used for assay techniques using plasmon excitation of proximal noble metal clusters, and the metal particles used for SEF, SERS, SERRS, or SPR.

In some embodiments, photosensitive glass is used to create metal nanoparticles beads. For example, metal oxides (e.g. silver) may be selectively reduced from the glass and coalesced into nanoparticles. In some embodiments, the initial glass composition is of: 65-72% silica, at least 3% $K_2O$ with 6%-16% of a combination of $K_2O$ and $Na_2O$, 0.15-5% of at least one oxide selected from the group consisting of $Ag_2O$ and $Au_2O$, 0.75%-7% $B_2O_3$, and 6-7% $Al_2O_3$, with the combination of $B_2O_3$, and $Al_2O_3$ not exceeding 13%, 8-13% $Li_2O$, and 0.014-0.1% $CeO_2$. In some embodiments, the composition is: 35-72% silica, 3-16% $K_2O$, 0.15-5% $Ag_2O$, 0.75-13% $B_2O_3$, 8-13% $Li_2O$, and 0.014-0.1% $CeO_2$. In some embodiments, the composition is 46-72% silica, 3-16% $K_2O$, 0.15-5% $Ag_2O$, 0.75-13% $B_2O_3$, 6-7% $Al_2O_3$, 11-13% $Li_2O$, and 0.014-0.1% $CeO_2$. Preferably in the above embodiments the $CeO_2$ is in the 0.04-0.1% range. In some embodiments, the glass substrate is heated to a temperature of 450-550° C. for between 10 minutes and 2 hours (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 hours or divisions thereof) and then heated to a temperature range heated to 550-650 C for between 10 minutes and 2 hours (e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 hours or divisions thereof). Note the heat treatment tends to crystallize the photosensitive glass, and that the "glass" as referred to herein, may be at least partially crystallized.

As noted above, the glass beads can be processed to provide enhanced sensitivity for biological-testing as compared to conventional surface areas of metal (e.g. areas of silver wire). However, the glass beads may also be exposed and etched to direct light within the glass beads substrate, e.g. on the backside of a structure of patterned nanoparticles for directing interrogation light and/or directing fluorescence from a patterned biological-binding area. In addition, a process exposure and etch can be used with our glass composition, and Kravitz el al's U.S. Pat. No. 7,132,054 is hereby incorporated by reference.

Apparently the only currently commercially available photosensitive glass is FOTURAN, made by Schott Corporation and imported into the U.S. only by Invenios Inc. FOTURAN comprises a lithium-aluminum-silicate glass containing traces of silver ions. When exposed to UV-light within the absorption band of the metal ion dopants in the glass, they act as sensitizer, absorbing a photon and stripping an electron that reduces neighboring silver ions to form colloidal silver atoms. These silver colloids provide nucleation sites for crystallization of the surrounding glass. If exposed to UV light through a mask, only the exposed regions of the glass will crystallize during subsequent heat treatment at a temperature greater than the glass transformation temperature (e.g., greater than 450 degree C. in air for FOTURAN). The crystalline phase is more soluble in hydrofluoric acid (HF) than the unexposed vitreous, amorphous regions. In particular, the crystalline regions of FOTURAN are etched about 20 times faster than the amorphous regions in 10% HF, enabling microstructures with wall slopes ratios of about 20:1 when the exposed regions are removed. See T. R. Dietrich et al., "Fabrication technologies for microsystems utilizing photoetchable glass," Microelectronic Engineering 30, 497 (1996), which is incorporated herein by reference. FOTURAN is described in information supplied by Invenios (the sole source U.S. supplier for Foturan) as composed of silicon oxide ($SiO_2$) of 75-85% by weight, lithium oxide ($Li_2O$) of 7-11% by weight, aluminum oxide ($Al_2O_3$) of 3-6% by weight, sodium oxide ($Na_2O$) of 1-2% by weight, 0.2-0.4% by weight antimony trioxide ($Sb_2O_3$), silver oxide ($Ag_2O$) of 0.05-0.15% by weight, and cerium oxide ($CeO_2$) of 0.01-0.04% by weight.

In some of the etched structure of the present invention (also called APEX composition) composed, by weight, of 71.66% silicon oxide ($SiO_2$), 0.75% boron oxide ($B_2O_3$), 0.4% antimony trioxide ($Sb_2O_3$), 11% lithium oxide ($Li_2O$), 6% aluminum oxide ($Al_2O_3$), 2% sodium oxide ($Na_2O$), 0.15% silver oxide ($Ag_2O$), and 0.04% cerium oxide ($CeO_2$) of by weight, and exposing one portion of the photosensitive glass substrate with ultraviolet light 305 to 315 nm light using an activation exposure of 9 $J/cm^2$, while leaving a second portion of said glass wafer unexposed. The glass substrate was heated to a temperature of 500° C. for one hour and then to a temperature of 600° C. for one hour and then cooled to transform at least part of the exposed glass to a crystalline material. The glass substrate was then etched in an HF-containing etchant solution. Surprisingly, while the composition in the above APEX-1 is similar to FOTURAN, our experiments with a glass of the above type showed a surprising sensitivity to ultraviolet light exposure of over three times that of the commercially available photosensitive glass (an exposure of 1 $J/cm^2$ was successfully used in a subsequent experiment), and a surprising over six times the etch rate as compared to FOTURAN when both compositions were processed in the way recommended for FOTURAN (with the sole exception of the reduced exposure level used for APEX-1 due to its greater sensitivity). Further, our glass had an etch ratio of exposed portion to that of the unexposed portion of about 50:1, while the best reported etch ratio of the commercially available FOTURAN photosensitive glass is about 30:1. The dramatically improved etch result due to the lower exposure leads to less light scattering into the side walls, and thus less etching of the side walls. The preferred composition modifications of adding boron oxide and reducing the silica content may lead to boron silicate formation that enhances crystallization, but in any case, the results are surprising.

Thus photosensitive glass can be processed to provide enhanced sensitivity for biological-testing and for directing interrogation light and/or directing fluorescence from a patterned biological-binding area. Thus the photosensitive glass may have patterned nanoparticles on one side and high precision etched structures on the other (although both could be on the same side).

The glass structure may also be patterned to create exposed regions of higher index of refraction surrounded by areas of lower index of refraction, such that light is substantially contained within the higher index of refraction material. Conversely, the patterned glass structure may be patterned to create exposed regions of higher index of refraction surrounding areas of lower index of refraction, such that light is substantially contained within the lower index of refraction material. Either way, exposing our glass with such ultraviolet light can raise index of refraction of the glass and such changed index of refraction may used to direct, manipulate, or process photons. Thus in some cases, etching of the glass is not necessary to direct light within such a glass structure.

In some embodiments, the patterned glass structure is processed by flood exposing to 300-320 nm light and baking to convert $Ce^{3+}$ in both previously process and non-previously processed regions to $Ce^{4+}$ to reduce the autofluorescence of cerium. The glass substrate may also be heated to a temperature in excess of the glass transformation temperature to allow at least part of the reduced noble metal to coalesce to provide a patterned glass structure that can be used to form larger clusters for at least one plasmon analytical technique, e.g. surface enhanced fluorescence, surface enhanced Raman spectroscopy, and surface plasmon resonance.

The present invention may be used to selectively bind DNA, RNA, PNA, lipids, antibodies, proteins, enzymes, drugs, pro-drugs, receptors, ligands, analytes, cells, bacteriophages, cell components, molecular imprint antibodies, DNA-based aptamers, cyclodextrins, macromolecules, dendrimers or other biological or synthetic compound, complex or composition.

In addition the present invention may be used in conjunction with labels e.g., cresyl fast violet, cresyl blue violet, rhodamine-6G, para-aminobenzoic acid, phthalic acids, erythrosin or aminoacridine. In addition, fluorophore or fluorescent reporter groups may be used and include any compound, label, or moiety that absorbs energy, typically from an illumination source, to reach an electronically excited state, and then emits energy, typically at a characteristic wavelength, to achieve a lower energy state, e.g., fluorescein and its derivatives; rhodamine and its derivatives; cyanine and its derivatives; coumarin and its derivatives; Cascade Blue™ and its derivatives; Lucifer Yellow and its derivatives; BODIPY and its derivatives; and the like. Exemplary fluorophores include indocarbocyanine (C3), inododicarbocyanine (C5), Cy3, Cy3.5, Cy5, Cy5.5, Cy7, Texas Red, Pacific Blue, Oregon Green 488, Alexa Fluor 488, Alexa Fluor 532, Alexa Fluor 546, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine™), carboxy tetramethylrhodamine (TAMRA™), carboxy-X-rhodamine (ROX™), LIZ™, VIC™, NED™, PET™, SYBR, PicoGreen, RiboGreen, and the like. Descriptions of fluorophores and their use, can be found in, among other places, R. Haugland, Handbook of Fluorescent Probes and Research Products, 9.sup.th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va. Near-infrared dyes are expressly within the intended meaning of the terms fluorophore and fluorescent reporter group.

In certain embodiments, detecting includes near field microscopy, near-field scanning optical microscopy; far-field microscopy, far-field confocal microscopy and fluorescence correlation spectroscopy; wide-field epi-illumination microscopy, evanescent wave excitation microscopy or total internal reflectance (TIR) microscopy; scanning confocal fluorescence microscopy; the multiparameter fluorescence detection (MFD) technique; two-photon excitation microscopy;

inverted optical microscope; or fluorescence excitation spectroscopy combined with shear-force microscopy.

In certain embodiments, detecting includes scanning probe microscopy techniques, applied optical spectroscopy techniques, nanoelectromechanical (NEMS) techniques, scanning tunneling microscopy; atomic force microscopy (AFM), cryo-AFM and single-walled carbon nanotube-AFM (SWNT-AFM); spectrally resolved fluorescence imaging microscopy (SFLIM); surface enhanced Raman spectroscopy (SERS); surface enhanced resonant Raman spectroscopy (SERRS); surface plasmon resonance (SPR); and scanning electrochemical microscopy (SECM).

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A method of providing a bead having discrete binding areas for biological-testing, comprising:
    preparing a glass bead substrate by at least one process step selected from the group consisting of
    exposing the glass bead to an activating energy source, baking the glass bead having a glass transition temperature at a temperature above the glass transition temperature, etching at least one selected area of the glass bead to expose metal nanoparticles from within the glass, wherein the metal nanoparticles have a range of diameters and are spaced from other metal nanoparticles by an average distance of at least one-half the midpoint of the diameter range, and the metal nanoparticles are less than about 300 nanometers in diameter, whereby the at least one selected area provides a chemistry for increased binding as compared to unselected areas.

2. The method of claim 1, wherein the metal nanoparticles comprise silver, gold, platinum, rhodium, palladium, nickel, cobalt, and copper, and alloys thereof.

3. The method of claim 1, wherein the metal nanoparticles comprise oxides of one or more metal oxides selected from silver, gold, and copper, and wherein at least some of the one or more metal oxides are reduced to metal to provide the metal nanoparticles.

4. The method of claim 1, wherein the glass bead substrate comprises one or more nucleating agents selected from titanium dioxide, tin oxide, ruthenium, rhenium, oxmium iridum, phosphorous pentoxide, Vanadium pentoxide, molybdenum oxides, tungsten oxides, iron oxides, and combinations thereof.

5. The method of claim 1, wherein the metal nanoparticles that are exposed from within the glass bead are formed by metal-precipitating and then metal-coalescing baking.

6. The method of claim 1, wherein the areas are exposed to high-energy particles to reduce at least some oxide of at least one of silver, gold, and copper in the areas to metal.

7. The method of claim 1, wherein the metal nanoparticles are added as metal particles during fabrication of the glass bead substrate.

8. The method of claim 1, wherein the metal nanoparticles are added as metal salt during fabrication of the glass bead substrate.

9. A substrate for binding biological molecules without pretreatment comprising:
    an at least partially spherical glass substrate comprising one or more metal particle regions that are exposed from within the at least partially spherical glass substrate, wherein the substrate is capable of binding biological molecules without pretreatment.

10. The substrate of claim 9, wherein the one or more metal particle regions comprise silver, gold, platinum, rhodium, palladium, nickel, cobalt, and copper, and alloys thereof.

11. The substrate of claim 9, wherein the one or more metal particle regions comprise oxides of one or more metal oxides selected from silver, gold, and copper, and wherein at least some of the one or more metal oxides are reduced to metal to provide metal nanoparticles.

12. The substrate of claim 9, wherein the one or more metal particle regions that are exposed from within the at least partially spherical glass substrate are formed by metal-precipitating and then metal-coalescing baking.

13. The substrate of claim 9, wherein the one or more metal particle regions are exposed to high-energy particles to reduce at least some oxide of at least one of silver, gold, and copper in the areas to metal.

14. The substrate of claim 9, wherein the one or more metal particle regions are added as metal particles during fabrication of the glass bead substrate.

15. The substrate of claim 9, wherein the one or more metal particle regions comprise a metal particle that is generally micrometer or nanometer in diameter.

16. The substrate of claim 9, wherein the one or more metal particle regions comprise metal nanoparticles, wherein the metal nanoparticles have a range of diameters and are spaced from other metal nanoparticles by an average distance of at least one-half the midpoint of the diameter range, and the metal nanoparticles are less than about 300 nanometers in diameter, whereby the one or more metal particle regions provide a chemistry for increased binding as compared to other areas of the substrate.

17. A micro-sphere binding assay for binding biological molecules without pretreatment comprising:
preparing a glass micro-sphere bead substrate by least one process step selected from the group consisting of exposing the glass micro-sphere bead to an activating energy source, baking the glass micro-sphere bead having a glass transition temperature at a temperature above the glass transition temperature, etching at least one selected area of the glass micro-sphere bead to expose metal nanoparticles from within the glass micro-sphere bead; and depositing patterned areas of biological-binding-glass on a substrate, wherein the metal nanoparticles have a range of diameters and are spaced from other metal nanoparticles by an average distance of at least one-half the midpoint of the diameter range, and the metal nanoparticles are less than about 300 nanometers in diameter, whereby the at least one selected area provides a chemistry for increased binding as compared to unselected areas;
binding one or more biological molecules to the glass micro-sphere bead; and
detecting the presence of the one or more biological molecules.

18. The assay of claim 17, wherein the metal nanoparticles are used for assay techniques using plasmon excitation of proximal noble metal clusters.

19. The assay of claim 17, wherein the metal nanoparticles are used for surface enhanced fluorescence SEF, surface enhanced Raman spectroscopy SERS, surface enhanced resonant Raman spectroscopy SERRS, or surface plasmon resonance SPR.

20. The assay of claim 17, wherein the metal nanoparticles comprise oxides of one or more metal oxides selected from silver, gold, and copper, and wherein at least some of the one or more metal oxides are reduced to metal to provide the metal nanoparticles.

21. The assay of claim 17, wherein the metal nanoparticles that are exposed from within the glass micro-sphere bead are formed by metal-precipitating and then metal-coalescing baking.

22. The assay of claim 17, wherein the at least one selected area is exposed to high-energy particles to reduce at least some oxide of at least one of silver, gold, and copper to metal in the at least one selected area.

23. The assay of claim 17, wherein the metal nanoparticles are added as metal particles during fabrication of the glass micro-sphere bead substrate.

24. The method of claim 17, wherein the metal nanoparticles are added as metal salt during fabrication of the glass micro-sphere bead substrate.

* * * * *